United States Patent
Kasahara

(10) Patent No.: US 12,405,232 B2
(45) Date of Patent: Sep. 2, 2025

(54) X-RAY INSPECTION APPARATUS USED FOR AN INSPECTION OF A SUBSTRATE, X-RAY INSPECTION SYSTEM, IMAGE MANAGEMENT METHOD AND PROGRAM

(71) Applicant: OMRON Corporation, Kyoto (JP)

(72) Inventor: Hironori Kasahara, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 452 days.

(21) Appl. No.: 17/967,079

(22) Filed: Oct. 17, 2022

(65) Prior Publication Data

US 2023/0046611 A1    Feb. 16, 2023

(30) Foreign Application Priority Data

Oct. 29, 2021    (JP) ................. 2021-177957

(51) Int. Cl.
| | |
|---|---|
| G01N 23/046 | (2018.01) |
| A61B 6/00 | (2006.01) |
| F04C 15/06 | (2006.01) |
| F04C 18/344 | (2006.01) |
| G03B 42/00 | (2021.01) |
| G06V 10/75 | (2022.01) |

(52) U.S. Cl.
CPC ............ *G01N 23/046* (2013.01); *A61B 6/44* (2013.01); *A61B 6/4429* (2013.01); *A61B 6/5205* (2013.01); *F04C 15/064* (2013.01); *F04C 18/3441* (2013.01); *G03B 42/00* (2013.01); *G06V 10/75* (2022.01); *F04C 2210/206* (2013.01); *F04C 2240/603* (2013.01)

(58) Field of Classification Search
None
See application file for complete search history.

(56) References Cited

U.S. PATENT DOCUMENTS

| | | | |
|---|---|---|---|
| 10,054,432 B2* | 8/2018 | Kasahara | G01N 23/083 |
| 2008/0075341 A1* | 3/2008 | Goto | H04N 5/765 |
| | | | 382/128 |
| 2017/0356859 A1* | 12/2017 | Sugita | G01N 23/046 |

(Continued)

FOREIGN PATENT DOCUMENTS

| | | |
|---|---|---|
| JP | 2007107966 A | 4/2007 |
| JP | 2008083830 A | 4/2008 |

(Continued)

OTHER PUBLICATIONS

Office Action issued in Japanese Appln. No. 2021-177957 mailed Jun. 24, 2025.

*Primary Examiner* — Tahmina N Ansari
(74) *Attorney, Agent, or Firm* — ROSSI, KIMMS & McDOWELL LLP

(57) ABSTRACT

An X-ray inspection apparatus is used for an inspection of a substrate, and the X-ray inspection apparatus includes an image acquisition unit that acquires a plurality of tomographic images for the substrate, an image extraction unit that extracts, from a data set obtained based on the plurality of tomographic images, an inspection tomographic image that is a target for determining whether the substrate is acceptable or not, a saved data generation unit that generates predetermined saved data including at least the inspection tomographic image, and a saved data storage unit that stores the saved data.

15 Claims, 6 Drawing Sheets

(56) References Cited

U.S. PATENT DOCUMENTS

| | | | |
|---|---|---|---|
| 2018/0080763 A1* | 3/2018 | Kasahara | G01B 11/2527 |
| 2019/0162522 A1* | 5/2019 | Hong | G01N 21/95 |
| 2023/0046611 A1* | 2/2023 | Kasahara | A61B 6/4429 |
| 2023/0290439 A1* | 9/2023 | Li | G06N 3/08 |

FOREIGN PATENT DOCUMENTS

| | | |
|---|---|---|
| JP | 2009014693 A | 1/2009 |
| JP | 2012021942 A | 2/2012 |
| JP | 2012237729 A | 12/2012 |
| JP | 2017223468 A | 12/2017 |

\* cited by examiner

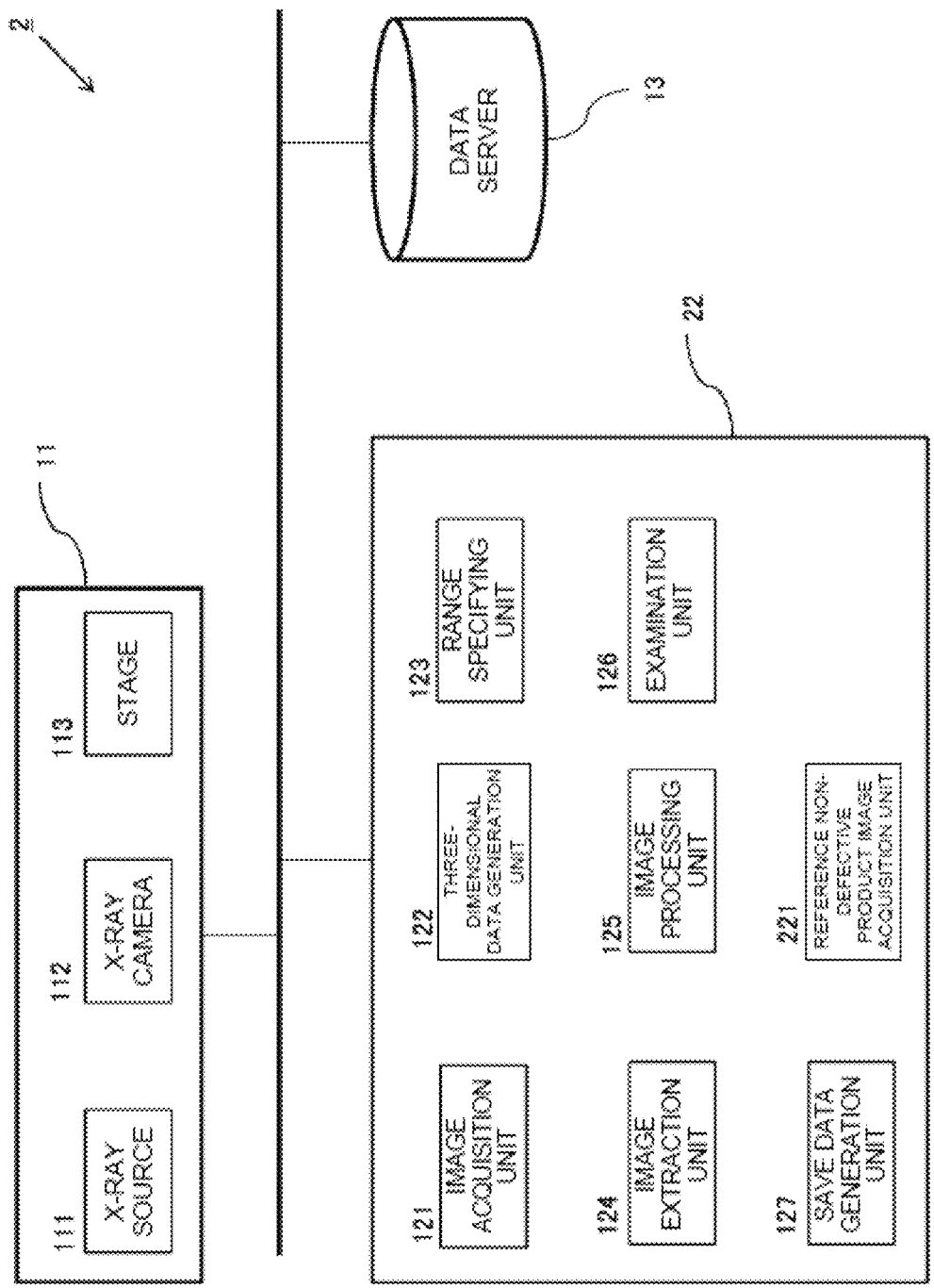

X-RAY INSPECTION APPARATUS USED FOR AN INSPECTION OF A SUBSTRATE, X-RAY INSPECTION SYSTEM, IMAGE MANAGEMENT METHOD AND PROGRAM

CROSS-REFERENCE TO RELATED APPLICATION

This application claims priority to Japanese Patent Application No. 2021-177957 filed on Oct. 29, 2021, the entire contents of which are incorporated herein by reference.

BACKGROUND

1. Technical Field

The present disclosure relates to an X-ray inspection apparatus, an X-ray inspection system, an image management method, and a recording medium.

2. Description of Related Art

Techniques for measuring the three-dimensional shape of an object by using an image taken when the object is irradiated with illumination light are known. The presence or absence or the type of a defect in the object is inspected by comparing the measured shape with a previously set determination criterion.

In recent years, size reduction and refinement of various products have caused an increase in the component packaging density of component mounted substrates etc. and have caused an increased number of sites that fall outside the field of view of an imaging device, and thus the number of components that cannot be inspected accurately by appearance inspection has increased. In contrast, a technique using X-ray computed tomography (CT) inspection to inspect a portion that cannot be inspected from the appearance is known (for example, Japanese Unexamined Patent Application Publication No. 2017-223468, hereinafter referred to as JP 2017-223468 A).

As in the technique disclosed in JP 2017-223468 A, in a case where the inspection is executed by acquiring the three-dimensional shape by X-ray CT inspection, a large number of sets of image data (for example, approximately 15 to 500) are acquired, a reconstruction process is performed based on the image data to acquire a three-dimensional CT image. Since the CT image is three-dimensional data, the size of the file output per inspection is large (for example, several tens of MB to several GB) as compared to two-dimensional image data. Meanwhile, from the viewpoint of traceability, etc., there is a need for long-term save of images used for the inspection and inspection results after the substrate is inspected. In this case, there is an issue of the need for a huge memory capacity in the case where large-volume files are saved for a long term as described above.

In this regard, Japanese Unexamined Patent Application Publication No. 2008-083830 (hereinafter, referred to as JP 2008-083830 A) discloses a technique for storing only needed medical images in the medical field. Specifically, JP 2008-083830 A discloses that a storage unit stores medical image data generated by a radiographic X-ray device, an MRI device, an ultrasound diagnosis device, etc., a predetermined number of tomographic images before and after the tomographic image corresponding to a key image are only left in the storage unit, and the other tomographic images are deleted from the storage unit (or compressed at a high compression rate) on a regular basis so that the capacity of the storage unit is secured. According to such a technique, it is possible to effectively use resources (the capacity of the storage area) while allowing for long-term save of needed medical images.

SUMMARY

In the technique disclosed in JP 2008-083830 A, although the image to be saved without deletion is determined based on the key image, the image selected for diagnosis by a physician or the image used by a radiologic technologist to create a diagnostic report is used as the key image for each individual inspection. That is, a person substantially decides which image is to be kept without deletion for each individual inspection.

However, in a case where a plurality of tomographic images is acquired for each of a large number of inspection objects (substrates) carried in a line, as in the inspection of a component mounted substrate, it is impractical for an operator to select the image to be saved for each individual inspection object (inspection target site thereof). That is, in the technique disclosed in JP 2008-083830 A, it is difficult to reduce the capacity of a storage device while achieving long-term save of images used for the inspection of a substrate.

An object of the present disclosure made in view of such circumstances is to provide the technique for reducing the storage capacity while saving the images used for the inspection on a long-term basis in the inspection of a component mounted substrate by using X-ray tomographic images.

To achieve the above-described object, the present disclosure adopts the following configuration. Specifically, an X-ray inspection apparatus is used for an inspection of a substrate, and the X-ray inspection apparatus includes an image acquisition unit that acquires a plurality of tomographic images for the substrate, an image extraction unit that extracts, from a data set obtained based on the plurality of tomographic images, an inspection tomographic image that is a target for determining whether the substrate is acceptable or not, a saved data generation unit that generates predetermined saved data including at least the inspection tomographic image, and a saved data storage unit that stores the saved data.

The "data set obtained based on the plurality of tomographic images" described above may be a set of imaging data itself obtained by taking the inspection object with X-rays or may be a data set (i.e., three-dimensional data) obtained by reconstruction processing based on a plurality of original images. The inspection tomographic image described above may be a processed image in which a specific cross-section is extracted (i.e., once processed image) from the data obtained by reconstruction processing based on the original image which is obtained by taking the inspection object with X-rays, or may be the original image itself representing the specific cross-section. A plurality of inspection tomographic images may be extracted from one inspection target.

According to this configuration, in the X-ray inspection of the substrate, it is possible to extract the tomographic image data that is the target for the inspection generate the data having a format including the image for the cross-section that is the target for the inspection, and exclusively save the generated data. Thus, it is possible to select the data to be saved from a plurality of sets of tomographic image data for each inspection without human intervention, and it is possible to save important images used for the inspection on a long-term basis while reducing the storage capacity in the X-ray inspection of the substrate to inspect a large number of inspection objects.

The X-ray inspection apparatus may further include a range specifying unit that specifies a predetermined range for an inspection target area of the substrate in the tomographic image. Here, the predetermined range for the inspection target area may cover individual portions of the substrate, such as solder portions, wiring pattern portions, or through-hole portions, but is not limited to these. The predetermined range for the inspection target area may be the entire tomographic image. According to this configuration, the range is specified in accordance with the site of the inspection target and the content of the defect to be detected, and then a predetermined process is performed for the specified range so that the inspection tomographic image may be efficiently extracted.

The image extraction unit may extract the inspection tomographic image based on an image feature value within the range specified by the range specifying unit. According to this configuration, the inspection tomographic image may be efficiently extracted by comparing the tomographic images. The information used by the image extraction unit to extract the inspection tomographic image is not limited to the image feature value. For example, the substrate may be measured by a laser displacement meter etc. and the inspection tomographic image may be extracted based on the measurement data, or the design information on the substrate may be acquired from a manufacturing device of the substrate and the inspection tomographic image may be extracted based on the design information.

The image extraction unit may extract, as the inspection tomographic image, an image including at least the range of the tomographic image having a largest value indicating variation in luminance within the range. Thus, it is possible to efficiently extract the cross-section suitable for acceptability determination in a case where, for example, a void inside the component is detected.

The image extraction unit may calculate a local feature value within the range, and extract an image including at least the range of the tomographic image having a largest value of the local feature value as the inspection tomographic image. The local feature value here is a feature value used for what is called edge detection and may be, for example, the degree of change in luminance in the image (e.g., the difference between a pixel in a certain portion and the surrounding pixel).

The X-ray inspection apparatus may further include a reference image acquisition unit that acquires a reference non-defective product image indicating the predetermined range of a non-defective product of the substrate, wherein the image extraction unit may perform pattern matching between the reference image and the predetermined range in the tomographic image, and may extract an image including at least the range of the tomographic image having a lowest matching rate of the pattern matching as the inspection tomographic image. According to this configuration, it is possible to efficiently extract the cross-section suitable for, for example, acceptability determination of a wiring pattern of the substrate.

The X-ray inspection apparatus may further include an image processing unit that executes predetermined image processing on the inspection tomographic image to generate a processed image, wherein the saved data may include the processed image.

For example, the image processing here includes binarization of the image and coloring of a specific element in the image in a specific color. By including the image processing unit, it is possible to generate and output the processed image with which the visibility of the state of the cross-section presented by the inspection tomographic image is improved.

The saved data may be one image file in which the inspection tomographic image and the processed image are arranged vertically or horizontally. According to this configuration, the inspection tomographic image and the processed image may be output and saved with a desired list form. Here, the processed image may be the one that is processed to improve the visibility of the state of the cross-section that is the inspection target, so that the element of the image used for acceptability determination may be easily checked, when the saved data is checked.

In addition to the inspection tomographic image and the processed image, the image file may present a numerical value indicating predetermined information about the inspection tomographic image and/or the processed image. Specifically, for example, it may be the value indicating the variation in luminance within the inspection tomographic image or may be the value indicating the matching rate of pattern matching with the non-defective product image. In a case where the processed image is generated by binarizing the inspection tomographic image, the value indicating the ratio of the area occupied by the pixel having one of the values in the processed image may be used. The image data may also be displayed together with the inspection result of acceptability determination.

The saved data may be a set of files including at least a file of the inspection tomographic image and a file of the processed image, and the files may be linked by name. The files may include a file indicating predetermined information about the inspection tomographic image and/or the processed image. According to this method, the information about one tomographic image may be collectively stored even though the saved data is not one set of image data.

The saved data generation unit may generate the saved data only for the substrate for which a result of the inspection indicates defective. According to this configuration, it is possible to reduce the data storage capacity more largely.

The present disclosure may also be regarded as an X-ray inspection system below. Specifically, an X-ray inspection system is used for an inspection of a substrate, and the X-ray inspection system includes an X-ray source that irradiates the substrate that is an inspection target with X-rays, an X-ray imaging unit that takes an X-ray tomographic image transmitted through the substrate, an image acquisition unit that acquires a plurality of tomographic images for the substrate, an image extraction unit that extracts, from a data set obtained based on the plurality of tomographic images, an inspection tomographic image that is a target for determining whether the substrate is acceptable or not, a saved data generation unit that generates predetermined saved data including at least the inspection tomographic image, and a saved data storage unit that stores the saved data.

The above-described X-ray inspection system may be configured as an X-ray inspection apparatus in which various units are integrated. Alternatively, a cloud system may be used, in which an element that performs X-ray radiography, an element that performs image processing, and a storage unit are configured separately and these components are connected by a communication unit.

The present disclosure may also be regarded as an image management method below. Specifically, an image management method for an X-ray inspection of a substrate includes acquiring a plurality of tomographic images for the substrate, extracting an inspection tomographic image that is a target for determining whether the substrate is acceptable or not from a data set obtained based on the plurality of tomographic images, acquiring information about an inspection result of the substrate, determining whether to generate predetermined saved data including at least the inspection tomographic image for each of a plurality of the substrates based on a predetermined processing condition corresponding to the inspection result, generating the saved data in a case where it is determined at the determining that the predetermined saved data is generated, and storing the generated saved data.

The present disclosure may also be regarded as a program causing a computer to implement the above-described method and a computer-readable recording medium storing the program in a non-transitory manner.

Each of the configurations and processes described above may be combined with each other to form the present disclosure as long as there is no technical contradiction.

According to the present disclosure, it is possible to provide the technique for reducing the storage capacity while saving the images used for the inspection on a long-term basis in the inspection of a component mounted substrate by using X-ray tomographic images.

BRIEF DESCRIPTION OF THE DRAWINGS

FIG. 6 is a block diagram illustrating a schematic configuration of an X-ray inspection system according to a modification of the first embodiment.

DETAILED DESCRIPTION OF EMBODIMENTS

Application Example

Configuration of Application Example

Figure 1:
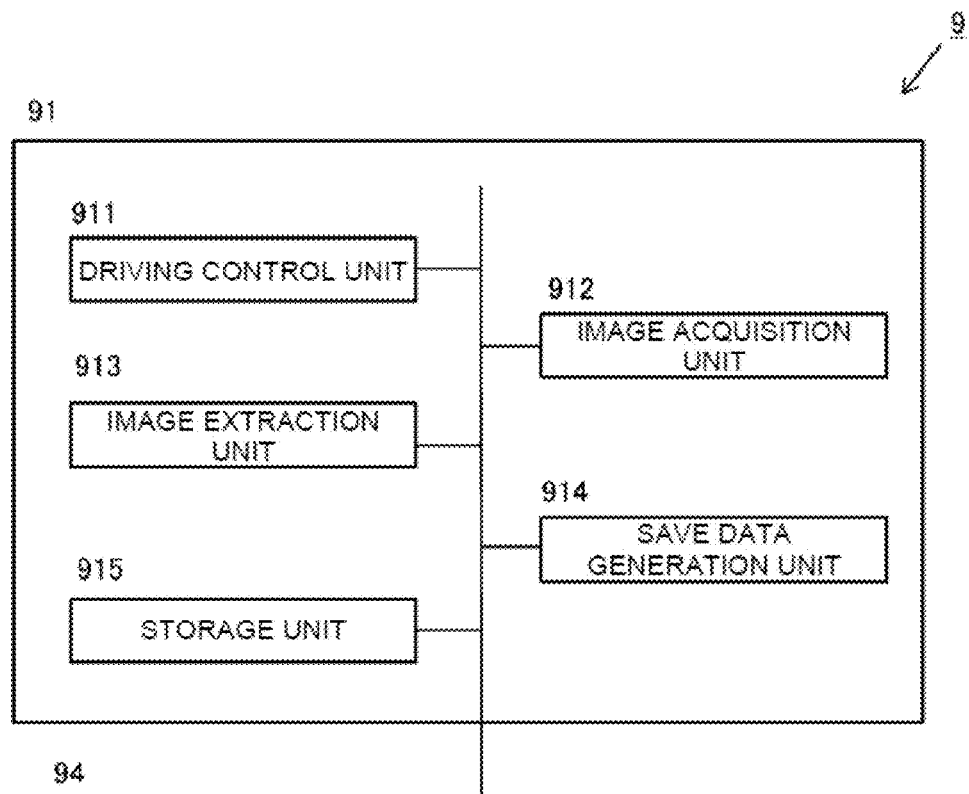
FIG. 1 is a schematic diagram illustrating a schematic configuration of an X-ray inspection apparatus according to an application example of the present disclosure.
Figure 1:
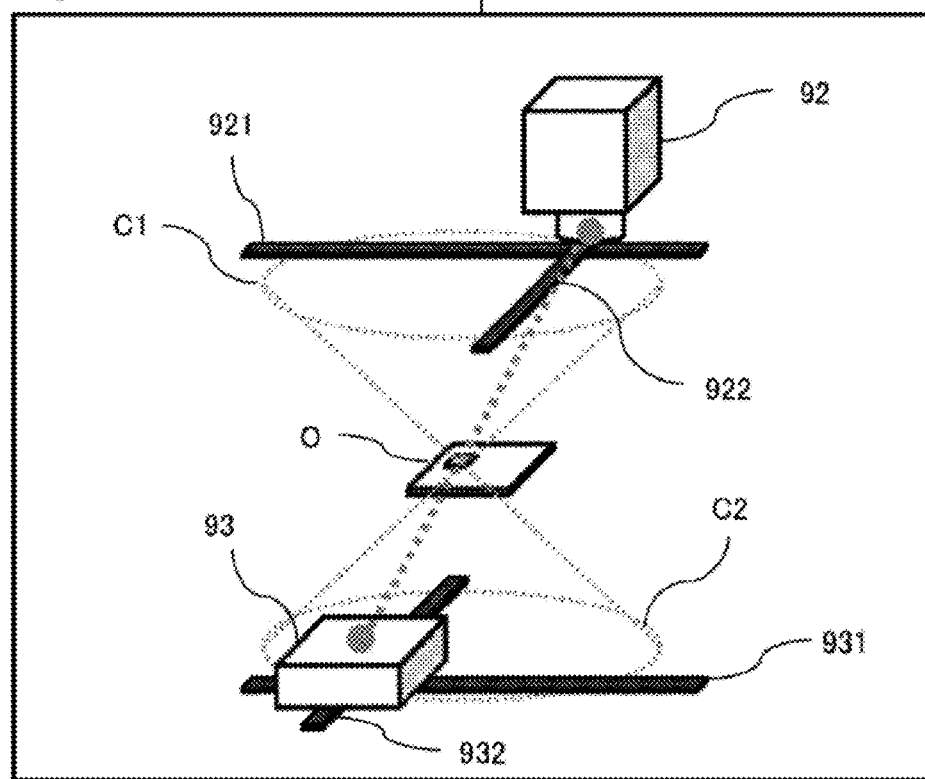

The following will describe an example according to an embodiment of the present disclosure. The present disclosure is applicable as, for example, an X-ray inspection apparatus that takes X-rays of a component mounted substrate, that is an inspection target and inspects the inspection target based on the captured image. FIG. 1 is a schematic diagram illustrating a schematic configuration of an X-ray inspection apparatus 9 according to this application example. The X-ray inspection apparatus 9 is typically configured to include a terminal 91 and an imaging unit 94 including an X-ray source 92 and an X-ray camera 93.

The terminal 91 may be configured by a general-purpose computer etc. and includes various functional units such as a driving control unit 911, an image acquisition unit 912, an image extraction unit 913, a saved data generation unit 914, and a storage unit 915. Although not illustrated, the terminal 91 further includes a three-dimensional data generation unit that reconstructs the three-dimensional shape of the target from a plurality of tomographic images captured by the X-ray camera 93, an inspection unit that determines whether a substrate O is acceptable or not based on the image data acquired from the X-ray camera 93 and a predetermined inspection criterion, various input units, and output units, etc.

The X-ray source 92 irradiates the substrate O that is conveyed by a conveyance roller (not illustrated) with X-rays. The X-ray camera 93 takes X-rays transmitted through the substrate O. The X-ray source 92 is movable by an X-stage 921 and a Y-stage 922. The X-ray camera 93 is movable by an X-stage 931 and a Y-stage 932. The X-ray source 92 and the X-ray camera 93 are moved by these stages in circular orbits C1 and C2, respectively, so that imaging is performed at a plurality of positions on the orbits.

The driving control unit 911 controls driving of each unit included in the X-ray inspection apparatus 9. Thus, the X-ray inspection apparatus 9 changes the relative positions of the substrate O, the X-ray source 92, and the X-ray camera 93 to capture the substrate O from a plurality of imaging positions. The image acquisition unit 912 acquires a plurality of sets of X-ray image data on the substrate O captured by the X-ray camera 93.

The image extraction unit 913 extracts, from a plurality of sets of original image data acquired by the image acquisition unit 912 or three-dimensional data reconstructed therefrom, an inspection tomographic image that is the target for determining whether the substrate is acceptable or not.

The saved data generation unit 914 generates predetermined saved data including at least the inspection tomographic image extracted by the image extraction unit 913. Specifically, it may be, for example, one set of image data indicating the inspection tomographic image and the value of the measurement result conducted for the inspection tomographic image, etc.

The storage unit 915 stores programs for controlling the inspection apparatus, imaging conditions, information (e.g., type, shape, dimension, and the like, of components) about the substrate O, and information about inspection criteria such as thresholds, etc. The storage unit 915 includes an area where the saved data generated by the saved data generation unit 914 is saved.

The following will explain an example of the flow of the process performed by the X-ray inspection apparatus 9 described above. First, the driving control unit 911 performs control to change the relative positions of the substrate O, the X-ray source 92, and the X-ray camera 93 to take X-rays from a plurality of different positions, and the image acquisition unit 912 acquires a plurality of sets of X-ray image data. Then, the image extraction unit 913 extracts, from the plurality of sets of original image data or the three-dimensional data reconstructed therefrom, the inspection tomographic image that is the target for determining whether the substrate is acceptable or not.

Then, the inspection is conducted by comparing the inspection tomographic image with a predetermined inspection criterion, and whether the substrate O is acceptable or not is determined. Furthermore, the saved data generation unit 914 generates the predetermined saved data including the inspection tomographic image. Then, the generated saved data is then saved in the storage unit 915. The saved data may be displayed on a liquid crystal display etc. that is an example of an output unit.

According to the X-ray inspection apparatus 9 of this application example, even if a large number of tomographic images are acquired for each inspection by the X-ray inspection apparatus, only the tomographic image used for the inspection which is a part of the large number of tomographic images can be saved data. Thus, it is possible to largely reduce the storage capacity for saving the image data for the inspection and reduce the cost for long-term save of inspection images.

First Embodiment

In the above application example, the X-ray inspection apparatus 9 is described as an example. The following will explain another embodiment for carrying out the present disclosure with reference to FIGS. 2 to 5.

System Configuration

Figure 2:
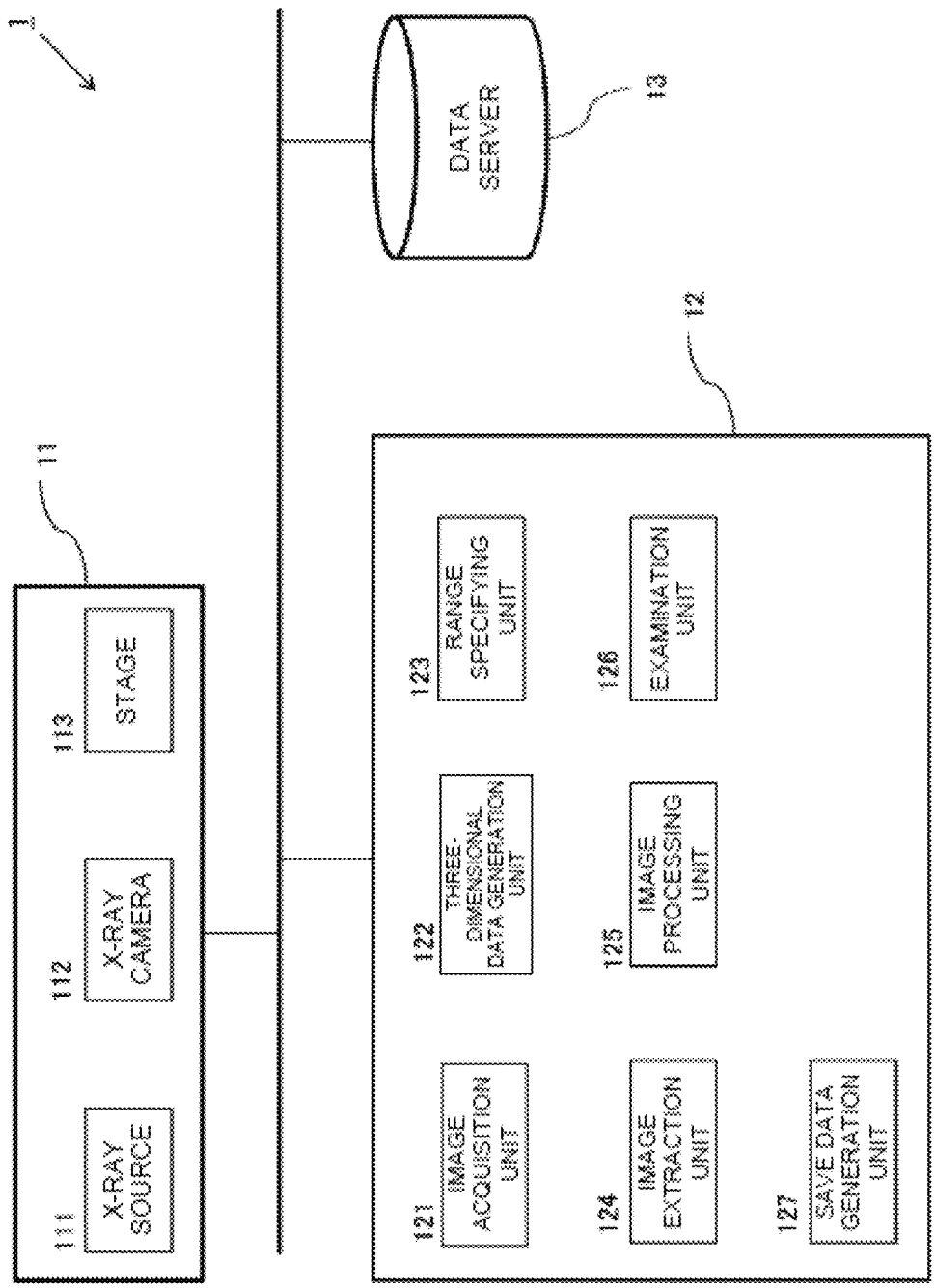
FIG. 2 is a block diagram illustrating a schematic configuration of an X-ray inspection system according to a first embodiment of the present disclosure.

FIG. 2 is a schematic block diagram illustrating a functional configuration of an X-ray inspection system 1 according to the present embodiment. The X-ray inspection system 1 according to the present embodiment is configured to include a radiographic X-ray device 11, an inspection terminal 12, and a data server 13. The X-ray inspection system 1 is an inspection system used for inspecting component mounted substrates. The radiographic X-ray device 11, the inspection terminal 12, and the data server 13 are connected to communicate with each other via a communication unit (not illustrated).

The radiographic X-ray device 11 includes an X-ray source 111, an X-ray camera 112, a stage 113 that holds the substrate, and a control unit (not illustrated) that controls these components, and each of these components may move relative to each other to capture tomographic images at different positions (and orientations) of the substrate. Since a desired known technology may be employed for the radiographic X-ray device 11, detailed descriptions of the X-ray source 111, the X-ray camera 112, the stage 113, and the like, are omitted.

Although not illustrated, the inspection terminal 12 may be a general-purpose computer including a processor such as a central processing unit (CPU) or a digital signal processor (DSP), etc., a storage unit, an input unit such as a keyboard and a mouse, and an output unit such as a liquid crystal display. The inspection terminal 12 may be configured by a single computer or a plurality of computers linked to each other.

For example, the above-described storage unit includes a primary storage unit such as a read-only memory (ROM) and a random access memory (RAM), and an auxiliary storage unit such as an Erasable Programmable Read Only Memory (EPROM), a hard disk drive (HDD) and removable media. The auxiliary storage unit of the storage unit stores an operating system (OS), various programs, and the like, and loads and executes the program in a working area of the primary storage unit, and the inspection terminal 12 is controlled through the execution of the program so that a functional unit that serves a predetermined purpose may be implemented as described below. Some or all of the functional units may be implemented by a hardware circuit such as an application specific integrated circuit (ASIC) or a field-programmable gate array (FPGA).

The data server 13 stores the imaging conditions of the radiographic X-ray device 11 (depending on the inspection content), information (e.g., type, shape, dimension, and the like, of components) about the inspection target substrate, information about the inspection criteria such as inspection items and thresholds, etc. The data server 13 is provided an area for storing the saved data generated by the inspection terminal 12 described below. The program for controlling the inspection terminal 12 may be stored in the data server 13.

Functional Unit of Inspection Terminal

Next, each functional unit included in the inspection terminal 12 will be described. The inspection terminal 12 includes various functional units such as an image acquisition unit 121, a three-dimensional data generation unit 122, a range specifying unit 123, an image extraction unit 124, an image processing unit 125, an inspection unit 126, and a saved data generation unit 127.

The image acquisition unit 121 acquires tomographic image data taken by the radiographic X-ray device 11. The image data may be acquired directly from the radiographic X-ray device 11, or the data once transmitted from the radiographic X-ray device 11 to the data server 13 and saved in the data server 13 may be acquired.

The three-dimensional data generation unit 122 generates data on the three-dimensional shape of the inspection target area (hereinafter also simply referred to as three-dimensional data) based on the acquired plurality of sets of X-ray tomographic image data. Since a known technology is applicable as the method for generating (constructing) the data, detailed descriptions are omitted.

The range specifying unit 123 specifies a predetermined range for the inspection target area of the substrate in the acquired tomographic image. For the predetermined range, the information previously set in accordance with the inspection target and the inspection content may be saved in the data server 13, or the like, and the information may be referred to to specify the area for each inspection. The predetermined range here may include, but not limited to, individual portions of the substrate, such as solder portions, wiring pattern portions, or through-hole portions. The predetermined range may be the entire tomographic image.

Figure 3A:
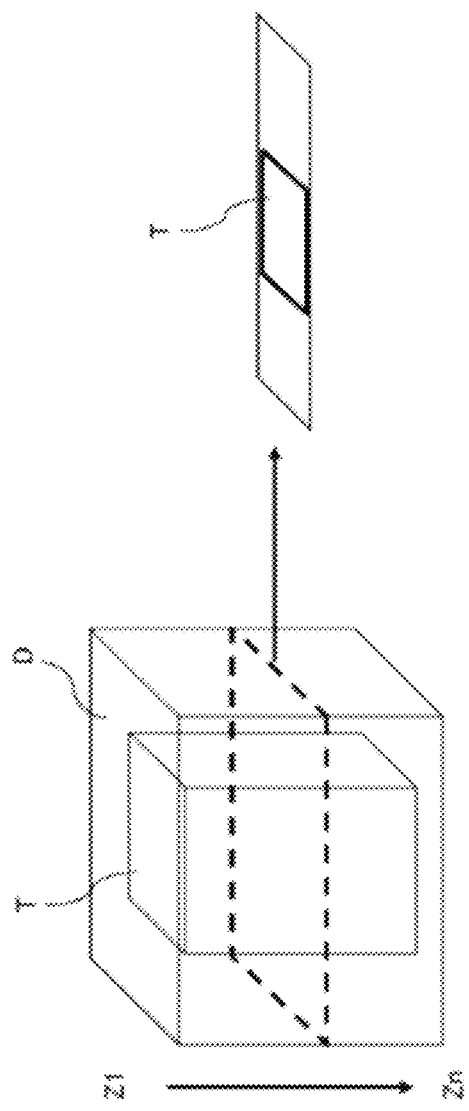
FIG. 3A is a first explanatory diagram illustrating a process performed by an image extraction unit according to the first embodiment of the present disclosure.
Figure 3B:
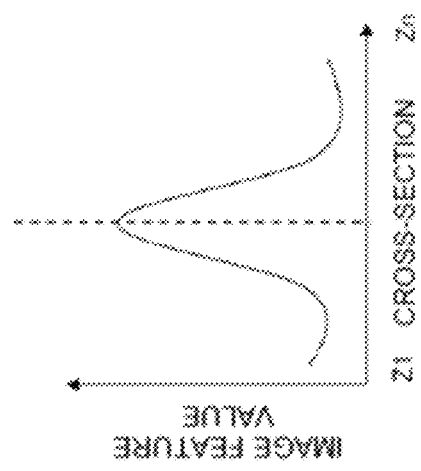
FIG. 3B is a second explanatory diagram illustrating the process performed by the image extraction unit according to the first embodiment of the present disclosure.
Figure 3C:
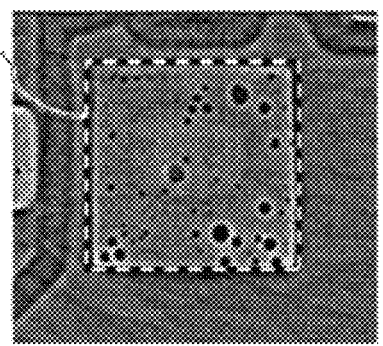
FIG. 3C is a third explanatory diagram illustrating the process performed by the image extraction unit according to the first embodiment of the present disclosure.

The image extraction unit 124 extracts, from the three-dimensional data generated by the three-dimensional data generation unit 122, the inspection tomographic image that is the target for determining whether the inspection target substrate is acceptable or not. An example of the extraction of the inspection tomographic image will be described with reference to FIGS. 3A to 3C. FIG. 3A is a diagram illustrating the relationship between three-dimensional data D reconstructed based on a plurality of tomographic images including a predetermined range T and an inspection tomographic image extracted therefrom. FIG. 3B is a histogram in which the X-axis indicates each cross-section in a Z-axis direction of the three-dimensional data and the Y-axis indicates the value of an image feature value in the predetermined range on each cross-section. FIG. 3C is a diagram illustrating an example of the extracted inspection tomographic image. The dashed lines illustrated in FIGS. 3A and 3B indicate the cross-section to be extracted.

For example, as illustrated in FIGS. 3A to 3C the image extraction unit 124 scans each cross-section of the three-dimensional data D generated by the three-dimensional data generation unit 122 to extract the tomographic image on the cross-section having the largest image feature value within the predetermined range T specified by the range specifying unit 123. For example, the image feature value here may be the value indicating the degree of variation in luminance within the predetermined range T.

The image processing unit 125 executes predetermined image processing on the extracted inspection tomographic image to generate a processed image. The image processing here includes, for example, binarization of the image and coloring of a specific element in the image in a specific color. For example, the inspection tomographic image may be represented in a mode different from that of a black-and-white X-ray tomographic image, such as the area representing a solder shape in light blue and the area representing a void in red. As a result, it is possible to generate the processed image with which the visibility of the state of the cross-section presented by the inspection tomographic image is improved.

The inspection unit 126 makes a decision whether the substrate is acceptable or not depending on whether the inspection tomographic image satisfies a predetermined inspection criterion in accordance with the inspection area and content. Specifically, this decision may be performed depending on whether the image feature value in the predetermined range specified by the range specifying unit 123 deviates from a predetermined threshold (inspection criterion), for example. The inspection result is transmitted to and saved in the data server 13. An inspection to determine whether the inspection target is acceptable or not may be separately executed by comparing the three-dimensional data itself with a predetermined inspection criterion.

Figure 4C:
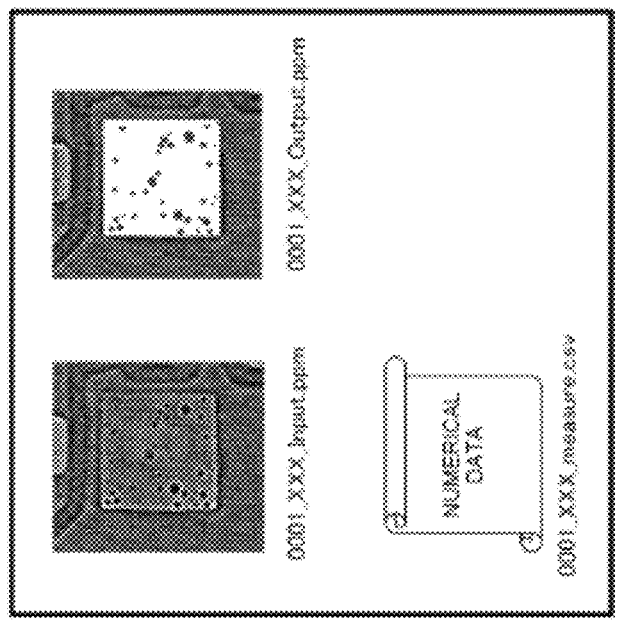
FIG. 4C is a third diagram illustrating an example of the content of the saved data according to the first embodiment of the present disclosure.
Figure 4B:
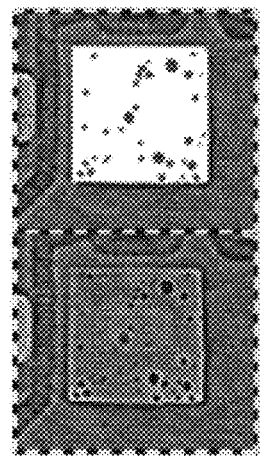
FIG. 4B is a second diagram illustrating an example of the content of the saved data according to the first embodiment of the present disclosure.
Figure 4A:
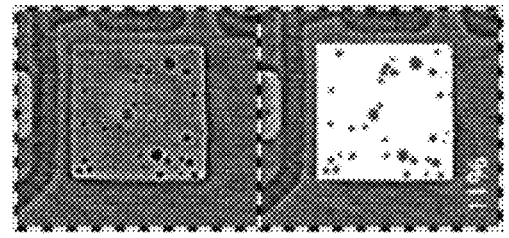
FIG. 4A is a first diagram illustrating an example of the content of saved data according to the first embodiment of the present disclosure.

The saved data generation unit 127 generates the saved data including the inspection tomographic image that is the inspection target and the processed image generated therefrom. FIGS. 4A to 4C illustrate an example of the content of the saved data. FIG. 4A is a first diagram illustrating an example of the content of the saved data. FIG. 4B is a second diagram illustrating an example of the content of the saved data. FIG. 4C is a third diagram illustrating an example of the content of the saved data. The processed image in each of the examples illustrated in FIGS. 4A to 4C is an image obtained by binarizing the predetermined range T of the inspection tomographic image, and the pixel represented by one of the binarized values (the pixel represented in dark color) indicates a void in the component that corresponds to the predetermined range T.

As illustrated in for example FIGS. 4A and 4B, the saved data may be generated as one image file in which the inspection tomographic image and the processed image are arranged side by side. As illustrated in FIG. 4A, the image file may also present the numerical value indicating predetermined information about the inspection tomographic image and the processed image. In the example in FIG. 4A, the processed image obtained by binarizing the predetermined range T of the inspection tomographic image presents the numerical value indicating the proportion of the pixels having one of the binarized values (i.e., the pixels indicating voids) within the predetermined range T. The numerical value may be presented by indicating, in the inspection tomographic image, the information about the image or by indicating, in both the inspection tomographic image and the processed image, the information about the respective images.

As illustrated in FIG. 4C, the saved data may be not only one image file but also a set (data set) of files linked by name. The character strings under the images in FIG. 4C represent examples of file names, and the part "XXX" is a common character string such as the component name.

The saved data generation unit 127 generates the saved data after determining whether to generate the saved data based on a predetermined condition that is previously set. The predetermined condition here means that, for example, the saved data is generated only for the inspection tomographic image (and its processed image) for which the inspection result by the inspection unit 126 indicates "defective." Alternatively, even if it is determined to be a "non-defective product," the saved data may be generated in the case where the feature value used for acceptability determination falls within a predetermined margin from the inspection criterion. Then, the saved data generated by the saved data generation unit 127 is saved in the data server 13.

Flow of Saved Data Generation Process

Figure 5:
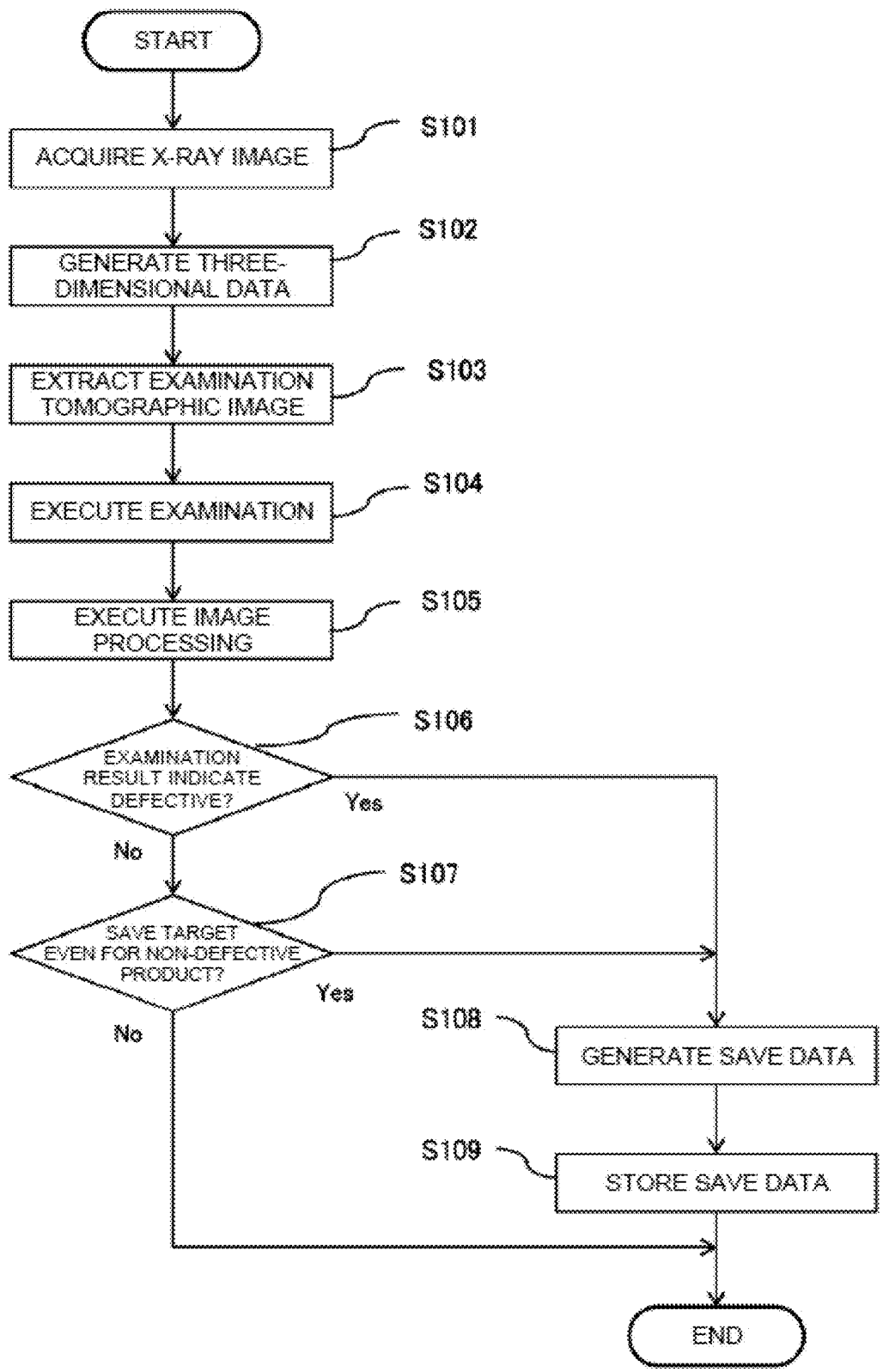
FIG. 5 is a flowchart illustrating an example of the flow of a process regarding saved data generation performed by the X-ray inspection system according to the first embodiment of the present disclosure.

Next, with reference to FIG. 5, the flow of the process from X-ray photography of the substrate that is the inspection target to the generation and storage of the saved data according to the present embodiment will be described. FIG. 5 is a flowchart illustrating an example of the flow of the process regarding the saved data generation process performed by the X-ray inspection system 1. At the start of the process, the radiographic X-ray device 11 takes an X-ray tomographic image of the substrate, and the image acquisition unit 121 acquires the X-ray tomographic image as illustrated in FIG. 5 (S101). Then, the three-dimensional data generation unit 122 generates the three-dimensional data of the site including the inspection target area from the plurality of X-ray tomographic images (S102).

Subsequently, the range specifying unit 123 specifies the predetermined range for the inspection target area of the substrate in the acquired tomographic image, and the image extraction unit 124 extracts the inspection tomographic image based on the image feature value in the predetermined range (S103). Furthermore, the inspection unit 126 executes an inspection to determine acceptability based on a predetermined inspection criterion for the extracted inspection tomographic image (S104). The image processing unit 125 executes predetermined image processing on the inspection tomographic image to generate a processed image (S105). The execution of inspection at step S104 corresponds to an inspection result acquisition step according to the present disclosure, and the execution order of steps S104 and S105 may be reversed.

Subsequently, the saved data generation unit 127 determines whether to generate the saved data including the inspection tomographic image and its processed image in accordance with the predetermined condition. Specifically, it is first determined whether the inspection result indicates defective (S106). In the case where it is determined to be defective, the process proceeds to step S108 to generate the saved data. On the other hand, in the case where it is determined to be non-defective at step S106, the process proceeds to step S107 to determine whether the inspection tomographic image is the target for the generation of the saved data even though it is a non-defective product (S107). Here, in the case where it is determined not to be the target for the generation of the saved data, the series of processes end. On the other hand, in the case where it is determined to be the target for the generation of the saved data at step S107, the process proceeds to step S108 to generate the saved data. Since an example of the determination criterion at step S107 has been described above, a description thereof is omitted.

The saved data generation unit 127 generates predetermined saved data for the inspection tomographic image for which it is determined that the saved data is to be generated as results of the determination processes at steps S106 and S107 (S108), the generated saved data is transmitted to the data server 13 and then stored in the predetermined storage area (S109), and the series of routines end. The saved data may be displayed on a liquid crystal display, or the like, before the saved data storage process at step S109.

According to the X-ray inspection system 1 as described above, even if a large number of tomographic images are acquired for each inspection, it is possible to largely reduce the storage capacity for saving the image data for the inspection and reduce the cost for long-term save of inspection images. A cloud system may achieve imaging of the substrate, inspection of the substrate, and save of the image used for the inspection.

Modification

According to the above first embodiment, though the variation in luminance is described as an example of the image feature value used by the image extraction unit to extract the inspection tomographic image, other image feature values may be used. FIG. 6 is a block diagram schematically illustrating an X-ray inspection system 2 using another image feature value instead of the variation in luminance according to a modification of the first embodiment. According to the present modification, identical reference numerals are used for configurations identical to those in the first embodiment, and detailed descriptions thereof are omitted.

As illustrated in FIG. 6, the X-ray inspection system 2 according to the present modification is different from the X-ray inspection system 1 only in that a reference non-defective product image acquisition unit 221 is included as a functional unit of an inspection terminal 22, and the other configurations are the same as those of the X-ray inspection system 1. The reference non-defective product image acquisition unit 221 acquires a reference non-defective product image that is an image indicating a predetermined range of a non-defective product of the inspection target substrate. The reference non-defective product image is previously stored in the data server 13 for each inspection target area, and the reference non-defective product image acquisition unit 221 may acquire the reference non-defective product image from the data server 13.

Then, the image extraction unit 124 performs pattern matching on each of the tomographic images representing each of cross-sections constituting the three-dimensional data with the reference non-defective product image and extracts, as the inspection tomographic image, the tomographic image having the lowest matching rate. That is, in the present modification, the matching rate of the pattern matching with the reference non-defective product image corresponds to the image feature value.

Although the reference non-defective product image is acquired from the data server 13 according to the above modification, the reference non-defective product image of a new substrate may be acquired from the radiographic X-ray device 11 at the time of start of inspection of the substrate.

Others

Each of the above examples merely illustrates the present disclosure, and the present disclosure is not limited to the above specific embodiments. Various modifications and combinations may be made to the present disclosure within the scope of the technical concept thereof. For example, other than the above, the degree of change in luminance in a predetermined range (e.g., the difference between the luminance of a pixel in a certain area and that of the surrounding pixel) may be used as the image feature value used by the image extraction unit to extract the inspection tomographic image.

The information used by the image extraction unit to extract the inspection tomographic image is not necessarily limited to the image feature values. For example, the substrate may be measured by a laser displacement meter etc. and the inspection tomographic image may be extracted based on the measurement data, or the design information on the substrate may be acquired from a manufacturing device of the substrate and the inspection tomographic image may be extracted based on the design information.

In the above embodiment, the case where one inspection tomographic image is extracted from one set of three-dimensional data has been described. However, a plurality of inspection tomographic images may be extracted from one set of three-dimensional data.

In the above embodiment, the saved data generation unit 127 determines whether to generate the saved data (steps S106 and S107). However, a configuration may be such that, instead of the determination process as described above, the saved data on the inspection tomographic image and the processed image are uniformly generated and output (transmitted to the data server and displayed on the liquid crystal display).

In the configuration according to each of the above examples, the imaging units such as the X-ray source and the X-ray camera are included, but the present disclosure is also applicable as an information processing terminal without such imaging unit as long as it is possible to acquire tomographic image data.

Note 1

An X-ray inspection apparatus (9) is used for an inspection of a substrate, and the X-ray inspection apparatus includes an image acquisition unit (912) that acquires a plurality of tomographic images for the substrate, an image extraction unit (913) that extracts, from a data set obtained based on the plurality of tomographic images, an inspection tomographic image that is a target for determining whether the substrate is acceptable or not, a saved data generation unit (914) that generates predetermined saved data including at least the inspection tomographic image, and a saved data storage unit (915) that stores the saved data.

Note 2

An X-ray inspection system (1) is used for an inspection of a substrate, and the X-ray inspection system includes an X-ray source (111) that irradiates the substrate that is an inspection target with X-rays, an X-ray imaging unit (112) that takes an X-ray tomographic image transmitted through the substrate, an image acquisition unit (121) that acquires a plurality of tomographic images for the substrate, an image extraction unit (124) that extracts, from a data set obtained based on the plurality of tomographic images, an inspection tomographic image that is a target for determining whether the substrate is acceptable or not, a saved data generation unit (127) that generates predetermined saved data including at least the inspection tomographic image, and a saved data storage unit (13) that stores the saved data.

Note 3

An image management method for an X-ray inspection of a substrate includes acquiring (S101) a plurality of tomographic images for the substrate, extracting (S103), from a data set obtained based on the plurality of tomographic images, an inspection tomographic image that is a target for determining whether the substrate is acceptable or not, acquiring (S104) information about an inspection result of the substrate, determining (S106, S107) whether to generate predetermined saved data including at least the inspection tomographic image for each of a plurality of the substrates based on a predetermined processing condition corresponding to the inspection result, generating (S108) the saved data in a case where it is determined at the determining that the predetermined saved data is generated, and storing (S109) the generated saved data.

What is claimed is:

1. An X-ray inspection apparatus used for an inspection of a substrate, the X-ray inspection apparatus comprising:
   (i) at least one memory configured to store computer-executable instructions and at least one processor configured to execute the computer-executable instructions stored in the at least one memory, (ii) at least one integrated circuit, or both (i) and (ii) that implement:
      an image acquisition unit that acquires a plurality of tomographic images for the substrate;
      an image extraction unit that extracts, from a data set obtained based on the plurality of tomographic images, an inspection tomographic image that is a target for determining whether the substrate is acceptable or not; and
      a saved data generation unit that generates predetermined saved data including at least the inspection tomographic image; and
   a saved data storage device that stores the saved data,
   wherein the saved data generation unit generates the saved data only for the substrate for which a result of the inspection indicates defective, and
   the saved data storage device stores the saved data on a long-term basis.

2. The X-ray inspection apparatus according to claim 1, wherein (i) the at least one memory configured to store computer-executable instructions and the at least one processor configured to execute the computer-executable instructions stored in the at least one memory, (ii) the at least one integrated circuit, or both (i) and (ii) further implement a range specifying unit that specifies a predetermined range for an inspection target area of the substrate in the tomographic image.

3. The X-ray inspection apparatus according to claim 2, wherein the image extraction unit extracts the inspection tomographic image based on an image feature value within the range specified by the range specifying unit.

4. The X-ray inspection apparatus according to claim 3, wherein the image extraction unit extracts, as the inspection tomographic image, an image including at least the range of the tomographic image having a largest value indicating variation in luminance within the range.

5. The X-ray inspection apparatus according to claim 3, wherein the image extraction unit calculates a local feature value within the range and extracts, as the inspection tomographic image, an image including at least the range of the tomographic image having a largest value of the local feature value.

6. The X-ray inspection apparatus according to claim 3, wherein (i) the at least one memory configured to store computer-executable instructions and the at least one processor configured to execute the computer-executable instructions stored in the at least one memory, (ii) the at least one integrated circuit, or both (i) and (ii) further implement a reference image acquisition unit that acquires a reference non-defective product image that is an image indicating the predetermined range of a non-defective product of the substrate, wherein
   the image extraction unit performs pattern matching between the reference non-defective product image and the predetermined range in the tomographic image and extracts, as the inspection tomographic image, an image including at least the range of the tomographic image having a lowest matching rate of the pattern matching.

7. The X-ray inspection apparatus according to claim 1, wherein (i) the at least one memory configured to store computer-executable instructions and the at least one processor configured to execute the computer-executable instructions stored in the at least one memory, (ii) the at least one integrated circuit, or both (i) and (ii) further implement an image processing unit that executes predetermined image processing on the inspection tomographic image to generate a processed image, wherein
   the saved data includes the processed image.

8. The X-ray inspection apparatus according to claim 7, wherein the saved data is one image file in which the inspection tomographic image and the processed image are arranged vertically or horizontally.

9. The X-ray inspection apparatus according to claim 8, wherein, in addition to the inspection tomographic image and the processed image, the image file presents a numerical value indicating predetermined information about the inspection tomographic image and/or the processed image.

10. The X-ray inspection apparatus according to claim 7, wherein the saved data is a set of files including at least a file of the inspection tomographic image and a file of the processed image, the files being linked by name.

11. The X-ray inspection apparatus according to claim 10, wherein the files include a file indicating predetermined information about the inspection tomographic image and/or the processed image.

12. An X-ray inspection system used for an inspection of a substrate, the X-ray inspection system comprising:
   an X-ray source that irradiates the substrate that is an inspection target with X-rays;
   an X-ray camera that takes an X-ray tomographic image transmitted through the substrate;
   (i) at least one memory configured to store computer-executable instructions and at least one processor configured to execute the computer-executable instructions stored in the at least one memory, (ii) at least one integrated circuit, or both (i) and (ii) that implement:
      an image acquisition unit that acquires a plurality of tomographic images for the substrate;
      an image extraction unit that extracts, from a data set obtained based on the plurality of tomographic images, an inspection tomographic image that is a target for determining whether the substrate is acceptable or not; and a saved data generation that generates predetermined saved data including at least the inspection tomographic image; and a saved data storage device that stores the saved data, wherein the saved data generation unit generates the saved data only for the substrate for which a result of the inspection indicates defective, and the saved data storage device stores the saved data on a long-term basis.

13. An image management method for an X-ray inspection of a substrate, the image management method comprising:

acquiring a plurality of tomographic images for the substrate;

extracting, from a data set obtained based on the plurality of tomographic images, an inspection tomographic image that is a target for determining whether the substrate is acceptable or not;

acquiring information about an inspection result of the substrate;

determining whether to generate predetermined saved data including at least the inspection tomographic image for the substrate based on a predetermined processing condition corresponding to the inspection result;

generating the saved data in a case where it is determined at the determining that the predetermined saved data is generated; and storing the generated saved data, wherein the saved data is generated only for the substrate for which a result of the inspection indicates defective, and the generated saved data is stored on a long-term basis.

14. A non-transitory computer-readable recording medium storing a program that causes a computer to execute the image management method according to claim 13.

15. The X-ray inspection apparatus according to claim 1, wherein the saved data generation unit is configured to acquire the result of the inspection of the substrate, to determine whether the acquired result indicates defective, and to generate the saved data only for the substrate for which the result of the inspection indicates defective.

* * * * *